United States Patent [19]
Hibino et al.

[11] Patent Number: 5,155,230
[45] Date of Patent: Oct. 13, 1992

[54] PHOTOCHROMIC DINITRATED SPIROPYRANS

[75] Inventors: Junichi Hibino, Hirakata; Eiji Ando, Katano, both of Japan

[73] Assignee: Matsushita Electric Industrial Co., Ltd., Osaka, Japan

[21] Appl. No.: 481,871

[22] Filed: Feb. 20, 1990

[30] Foreign Application Priority Data

Feb. 27, 1989 [JP] Japan ................................. 1-45997

[51] Int. Cl.$^5$ .................. C07D 491/107; G03C 1/685
[52] U.S. Cl. ................................................. 548/409
[58] Field of Search ........................................ 548/409

[56] References Cited

U.S. PATENT DOCUMENTS

| | | | |
|---|---|---|---|
| 3,212,898 | 10/1965 | Gerreta | 548/409 |
| 3,532,638 | 10/1972 | Otis | 252/300 |
| 3,773,508 | 11/1973 | Osuda et al. | 96/48 R |

FOREIGN PATENT DOCUMENTS

| | | |
|---|---|---|
| 2114747 | 11/1971 | France . |
| 244533 | 12/1978 | France . |
| 2445334 | 12/1978 | France . |

OTHER PUBLICATIONS

Arsenor, Chem. Abs., 108, 169151j, (1987).
Bulletin de la Societe Chim de France, No. 5, 1968, pp. 2066-2074 A. Hinnen et al. "Photo des indol, I. Syn. des Products".
M. Morin et al., "Spectral and Photochromic Properties of Two Long-Chain Spiropyranindoline Monolayers at the Air-Solid Interface", Can. Chem., vol. 58, pp. 2038-2043, 1980.
Samoilava, Chemical Abstracts, vol. 83, p. 818, Jul. 7, 1975.

*Primary Examiner*—Mark L. Berch
*Attorney, Agent, or Firm*—Ratner & Prestia

[57] ABSTRACT

The present invention provides a photochromic material possessing absorption sensitivity in a longer wavelength region when compared with conventional photochromic materials. The photochromic material is a spiropyran compound having a methoxy group at the 6 position, nitro groups at the 8 and 5' positions, and an alkyl group at the 1' position of the spiropyran skeleton as shown below:

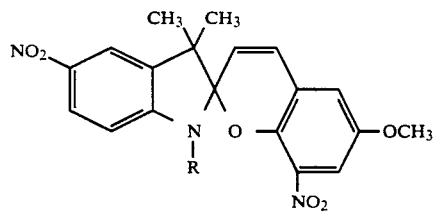

1 Claim, 1 Drawing Sheet

PHOTOCHROMIC DINITRATED SPIROPYRANS

BACKGROUND OF THE INVENTION

1. Field of the invention

The present invention relates to a photochromic material for use in optical storage media and other areas of application.

2. Description of Prior Art

Substances which display reversible color changes upon exposure to light are collectively known as photochromic materials. Spiropyran compounds constitute one of the most intensively studied types of photochromic material.

Many spiropyran compounds have already been reported in literatures. For example, the colorless spiropyran compound A of the following formula is transformed into the red compound merocyanine B by irradiation with ultraviolet rays of wavelength approximately 340 nm. The compound B reverts to the form A if irradiated with visible light with a wavelength of approximately 580 nm.

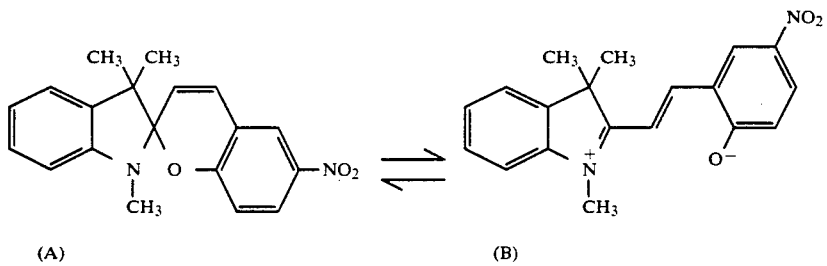

(A)        (B)

Optical storage media can be prepared by utilizing these photochromic materials which change their structures by irradiation. In order to miniaturize devices containing optical storage media, the use of semiconductor lasers is generally desirable. The semiconductor lasers employed in optical storage devices ordinarily emit light in a wavelength region in the neighborhood of 700 nm, and therefore the colored form of photochromic materials used for such purposes should desirably possess absorption sensitivity in this wavelength region.

SUMMARY OF THE INVENTION

The present invention, which overcomes the above-discussed and numerous other disadvantages and deficiencies of the prior art, provides a photochromic material consisting of a spiropyran compound of formula I:

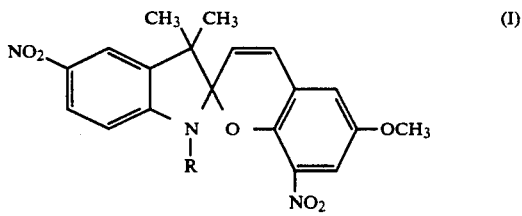

wherein R is alkyl containing 1 to 30 carbon atoms.

Thus, the invention described herein makes possible the objective of providing a photochromic material possessing absorption sensitivity in the long wavelength region, in particular, possessing absorption sensitivity at wavelengths in the length region of about 700 nm which is the wavelength of light emitted from conventional semiconductor laser devices, and displaying reversible color changes by irradiation with light of such wavelengths.

BRIEF DESCRIPTION OF THE DRAWING

This invention may be better understood and its numerous objects and advantages will become apparent to those skilled in the art by reference to the accompanying drawing as follows.

DESCRIPTION OF THE PREFERRED EMBODIMENT

Figure 1:
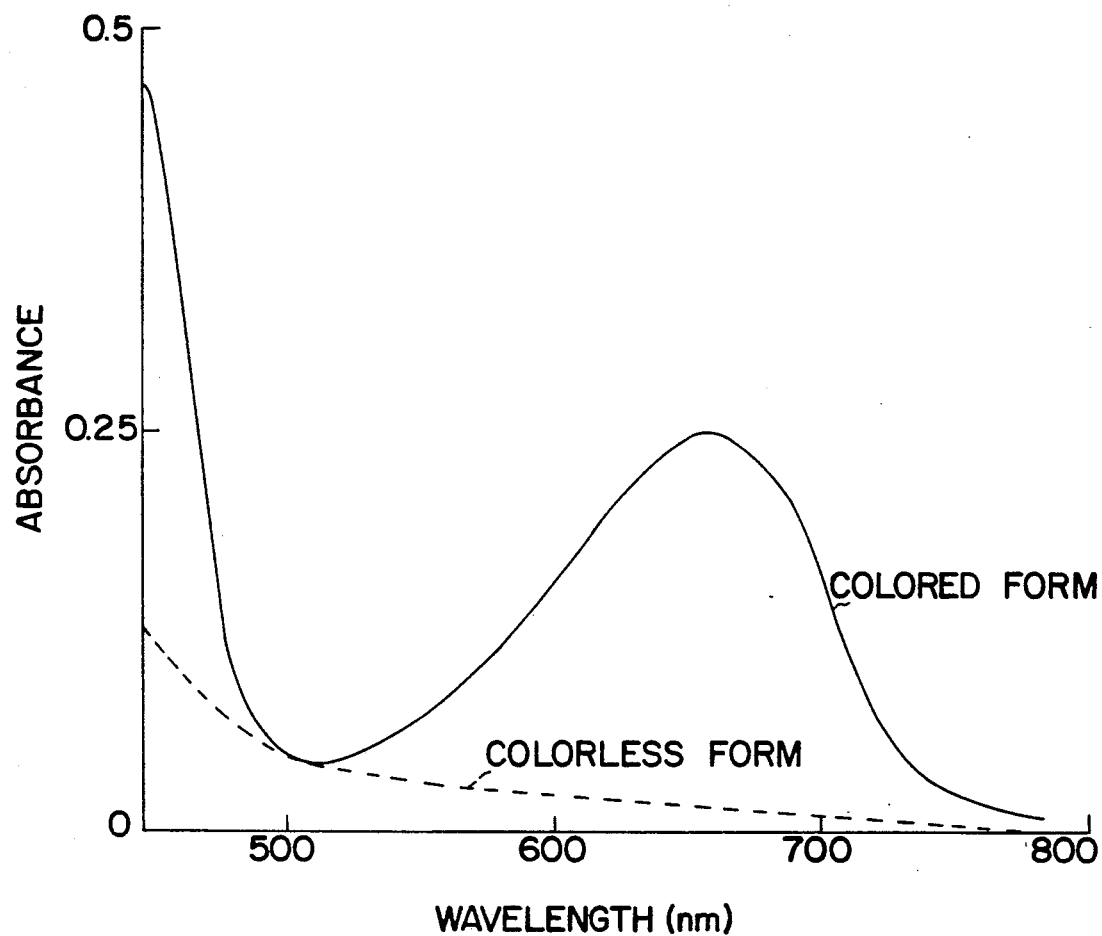
FIG. 1 shows the ultraviolet and visible absorption spectra in methanol of the colorless form and colored form of the spiropyran compound NSP1801b prepared in Example of this invention.

The photochromic material of the present invention is a specific spiropyran compound having nitro groups at the 8 and the 5' positions, a methoxy group at the 6 position, and an alkyl group at the 1' position of the spiropyran skeleton.

EXAMPLE

As the spiropyran compound of the present invention, a compound shown by the formula II, is exemplified (hereinafter referred to as NSP1801b).

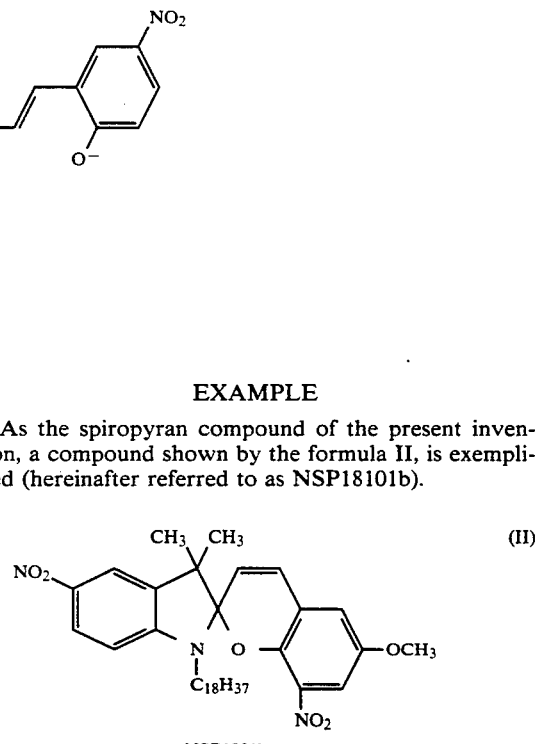

NSP1801b

A method for the preparation of the spiropyran compound NSP1801b will be described below.

Step 1

First, 42.3 g (266 mmol) of 2,3,3-trimethyl indolenine 1 and 101.1 g (266 mmol) of iodooctadecane 2 were dissolved in 200 ml of 2-butanone, then the mixture was heated and refluxed for 40 hours. After distilling off the 2-butanone, the solid residue was recrystallized from 1000 ml of ethanol, thereby obtaining 91.5 g (197 mmol, yield 63.9%) of 1-octadecyl-2,3,3-trimethylindolenium iodide 3 in the form of a reddish-white solid. This reaction can be expressed by the following chemical equation:

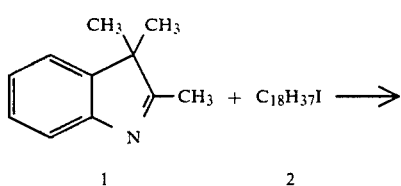

Step 2

First 91.5 g (197 mmol) of 1-octadecyl-2,3, 3-trimethylindolenium iodide 3 obtained in Step 1 was dispersed in 100 ml of diethylether, and this in turn was dispersed in 400 ml of a 3.8 N aqueous solution of sodium hydroxide. This suspension was then agitated for 3.5 hours, after which the oily layer was extracted with diethyl ether. After being dried over sodium hydroxide for 24 hours, the diethyl ether was distilled off, thereby obtaining 65.6 g (159 mmol, yield 80.7%) of 1-octadecyl-2-methylene-3,3-dimethylindoline 4 in the form of a yellow liquid. This reaction can be expressed by the following chemical equation:

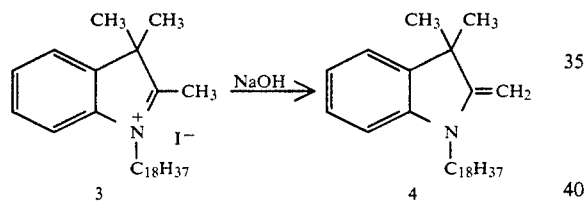

Step 3

First, 8.0 g (52.6 mmol) of 5-methoxysalicylaldehyde 5 was dissolved in 50 ml of acetic acid. Then, a mixed solution of 2.5 ml (59.7 mmol) of fuming nitric acid (99%, specific gravity 1.52) and 8 ml of acetic acid was added dropwise into the above mixture over a period of 1 hour while maintaining the temperature of the reaction mixture at approximately 15° C. with ice-cold water and strongly agitating the reaction mixture. Agitation was further continued for 7 hours. The precipitate formed was filtered, after which the precipitate was recrystallized from 500 ml of ethanol, thereby obtaining 4.2 g (21.3 mmol, yield 40.5%) of 3-nitro-5-methoxysalicylaldehyde 6 in the form of yellow needle crystals. This reaction can be expressed by the following chemical equation:

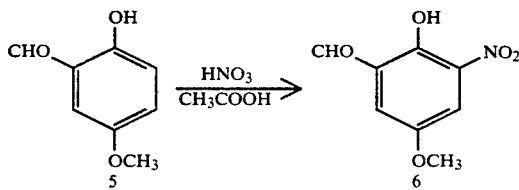

Step 4

First, 2 g (4.9 mmol) of 1-octadecyl-2-methylene-3,3-dimethylindoline 4 obtained in Step 2 and 0.8 g (4.1 mmol) of 3-nitro-5-methoxysalicylaldehyde 6 obtained in Step 3 were heated and refluxed in 20 ml of ethanol for 1 hour. The deep green reaction mixture was then cooled and the precipitate so obtained was recrystallized three times from 80 ml of ethanol, thereby obtaining 1.6 g (2.7 mmol, yield 65.9%) of the spiropyran compound 7 (yellowish-brown crystals). This spiropyran compound 7 possesses a methoxy group at the 6 position, a nitro group at the 8 position and an octadecyl group at the 1' position of the spiropyran skeleton. This reaction can be expressed by the following chemical equation:

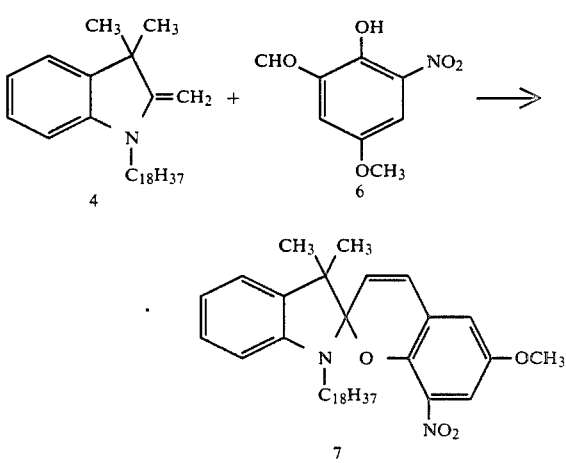

Step 5

First, 1.6 g (2.7 mmol) of the spiropyran compound 7 obtained in Step 4 above was dissolved in 10 ml of acetic acid. Then a mixed solution of 0.25 ml (6.0 mmol) of fuming nitric acid (99%, specific gravity 1.52) and 1 ml of acetic acid was added dropwise to the above mixture over a period of 30 minutes. One hour later, this reaction mixture was poured into a mixture of hexane and an aqueous solution of sodium hydroxide. The organic (hexane) layer was separated, and the water layer was extracted with hexane. The combined organic layer was dried, concentrated and then purified by the use of column chromatography. The purified product was then recrystallized twice from ethanol, thereby obtaining 300 mg of the spiropyran compound NSP1801b. This reaction can be expressed by the following chemical equation:

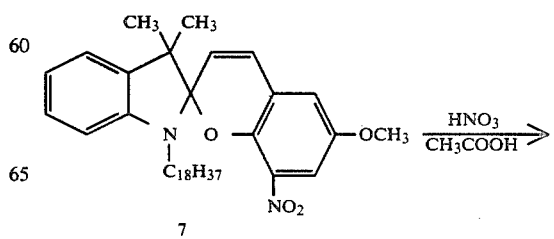

-continued

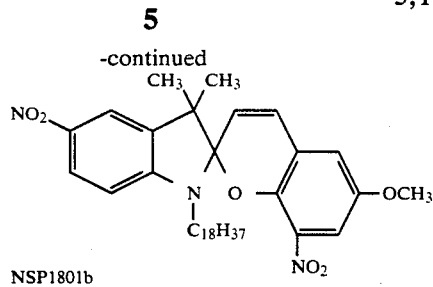

NSP1801b

The proton NMR spectrum was measured in order to verify the structure of the reaction product. The result of the measurement is shown in Table 1.

TABLE 1

| Chemical shift δ (ppm) | Multiplicity | Assignment | Number of protons |
|---|---|---|---|
| 0.88 | t | terminal methyl of long-chain alkyl J = 5.1 Hz | 3 |
| 1.20 | s | 3'-methyl | 3 |
| 1.25 | m | methylenes in long-chain alkyls | 32 |
| 1.38 | s | 3'-methyl | 3 |
| 3.24 | t | methylene binding to the nitrogen of indoline skeleton J = 7.1 Hz | 2 |
| 3.80 | s | methoxy | 3 |
| 5.85 | d | 3-olefin J = 10.3 Hz | 1 |
| 6.49 | d | 7'-H J = 8.6 Hz | 1 |
| 6.68 | d | 4-olefin J = 10.3 Hz | 1 |
| 6.90 | s | 5-H | 1 |
| 7.24 | s | 7-H | 1 |
| 7.92 | s | 4'-H | 1 |
| 8.14 | d | 6'-H J = 8.6 Hz | 1 |

In Table 1, the values of chemical shift were measured using TMS as a standard, and multiplicity indicated represents the form of each peak, with "s" denoting singlet, "d" doublet, "t" triplet and "m" multiplet.

The spiropyran compound NSP1801b obtained above was dissolved in ethanol. The solution was initially colorless, and was rapidly colored by irradiation with ultraviolet rays of 366 nm. The colored form of this spiropyran compound possesses an absorption maximum at 660 nm, and can absorb the light of 700 nm emitted by semiconductor lasers. FIG. 1 shows the ultraviolet and visible absorption spectra of the colorless and colored form of this compound. A thin film, that has the same absorption sensitivity at wavelengths in the region of about 700 nm as the solution in ethyl alcohol, was obtained from the solution of NSP 1801 b in ethyl alcohol by the spin coat method.

Spiropyran compounds having a methyl, octyl and triacontyl group at the 1' position are obtained using iodomethane, indooctane and indotriacontane instead of iodooctadecane respectively. The wavelengths of the absorption maxima of colored forms of these various compounds in ethanol are shown in Table 2.

TABLE 2

| Absorption maxima of various spiropyran compounds | |
|---|---|
| Substituent at 1' position | Absorption maximum (nm) |
| methyl | 658 |
| octyl | 660 |
| triacontyl | 662 |

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A photochromic material consisting of a spiropyran compound of formula I:

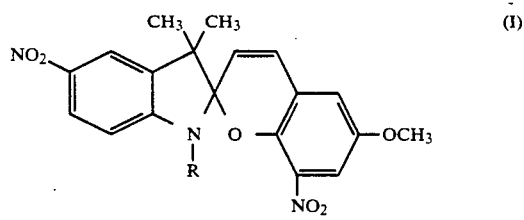

wherein R is alkyl containing 8 to 30 carbon atoms.

* * * * *